（12）United States Patent
Leyva

(10) Patent No.: US 8,376,939 B1
(45) Date of Patent: Feb. 19, 2013

(54) CORONARY ARTERY RETRACTION AND $CO_2$ DISPENSING DEVICE

(76) Inventor: Alberto David Leyva, Miami, FL (US)

( * ) Notice: Subject to any disclaimer, the term of this patent is extended or adjusted under 35 U.S.C. 154(b) by 138 days.

(21) Appl. No.: 12/855,002

(22) Filed: Aug. 12, 2010

Related U.S. Application Data

(60) Provisional application No. 61/235,221, filed on Aug. 19, 2009.

(51) Int. Cl.
*A61B 1/32* (2006.01)
*A61M 37/00* (2006.01)

(52) U.S. Cl. .......................... 600/205; 604/26

(58) Field of Classification Search .................... 604/23, 604/26; 600/200, 217, 201–210
See application file for complete search history.

(56) References Cited

U.S. PATENT DOCUMENTS

| | | | | |
|---|---|---|---|---|
| 5,139,478 A | * | 8/1992 | Koninckx et al. | 604/26 |
| 6,394,951 B1 | * | 5/2002 | Taylor et al. | 600/210 |
| 6,994,669 B1 | * | 2/2006 | Gannoe et al. | 600/232 |

* cited by examiner

*Primary Examiner* — Kevin C Sirmons
*Assistant Examiner* — Bradley Osinski
(74) *Attorney, Agent, or Firm* — Gold & Rizvi, P.A.; H. John Rizvi

(57) ABSTRACT

The present invention is referred to a coronary artery retraction means for retracting tissue and/or fat from the coronary artery during coronary anastomosis and a $CO_2$ supplying device capable of blowing $CO_2$ on the coronary artery during a bypass procedure while the retracting means holds and keeps the fat away from the artery. This device comprises, in one embodiment, a stainless steel 'V'-shaped wire, including a couple of elastic arms, which end with a hook-like retracting means, and also including on said arms grabbing means allowing the surgeon to place the device in place in an easy and fast maneuver, and a $CO_2$ supplying means on each arm, including at least one gas intake on one end and a gas outlet over said retracting means. In a second embodiment, all the different parts of the device define an integral piece made of plastic material which is fully disposable after the procedure.

20 Claims, 7 Drawing Sheets

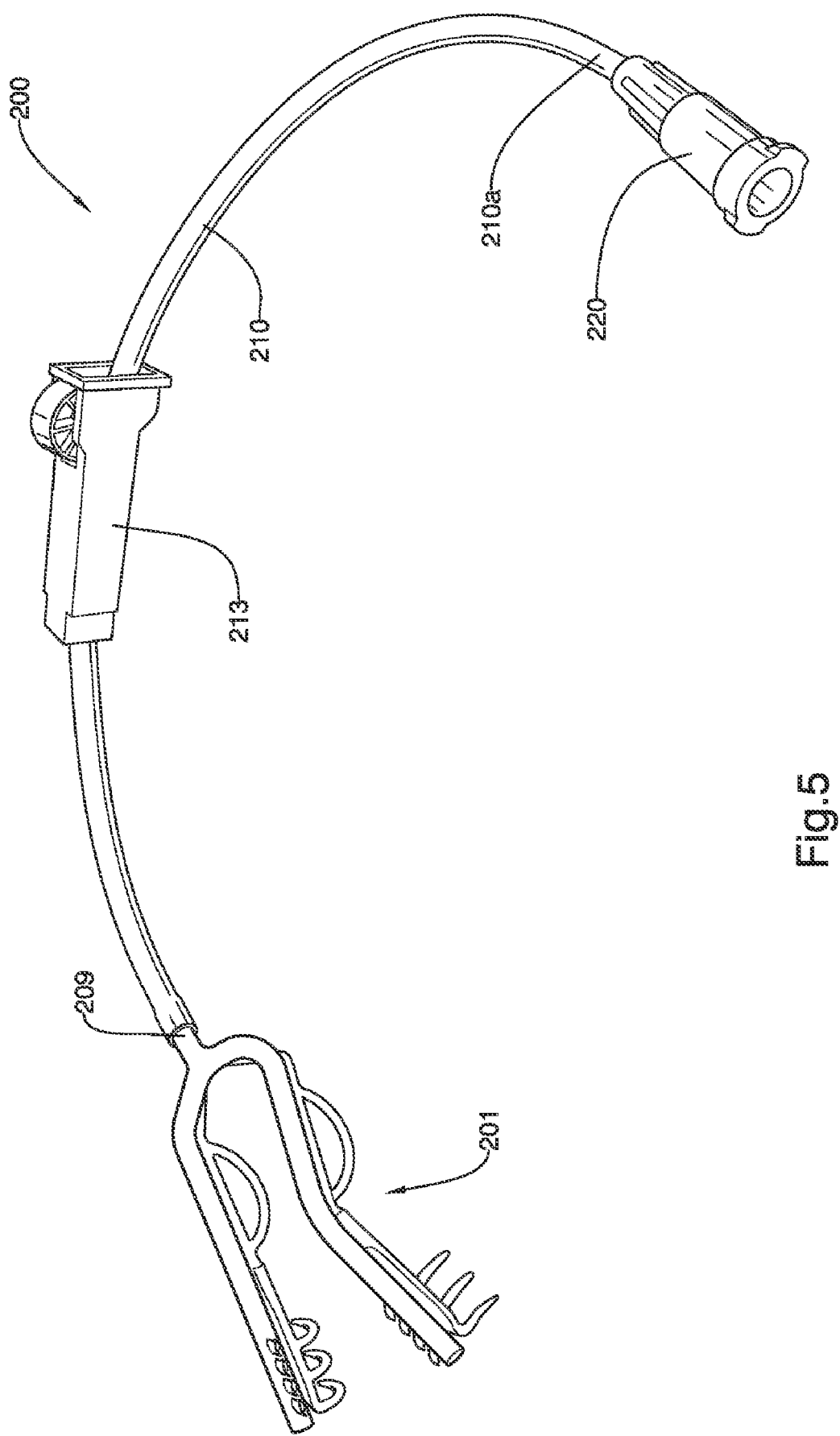

CORONARY ARTERY RETRACTION AND CO₂ DISPENSING DEVICE

CROSS-REFERENCE TO RELATED APPLICATION

This application claims the benefit of co-pending U.S. Provisional Patent Application Ser. No. 61/235,221, filed on Aug. 19, 2009, which is incorporated herein in its entirety.

BACKGROUND OF THE INVENTION

1. Field of the Invention

This invention relates generally to a surgery device that provides a fat and tissue retraction function and at the same time CO, supplying on the surgical field during a by-pass procedure. More particularly, the present invention is referred to a coronary artery retraction device that includes, as an integral part of its structure, a $CO_2$ supplying means basically comprising a conduit integral with the elastic arms of the retractor, including a special oriented outflow that directs the $CO_2$ flow on the surgical field, and a flow-controlling means for regulating the $CO_2$ flow. Even more particularly, the present invention purposes a coronary artery retraction and $CO_2$ dispensing device with which the by-pass surgical procedure is improved by reducing the number of hands necessary on the surgical field at the same time, reducing surgical risks and human errors.

2. Description of the Prior Art

Just like any other organ in the human body, the heart needs blood and oxygen to do its job. This blood is received through different vessels called arteries and veins. One of the main arteries is the coronary artery that snakes across the surface of the heart, delivering a constant supply of blood and oxygen to the heart muscle. When one or more of these arteries become narrowed or blocked, blood and oxygen are reduced, and heart muscle is damaged.

By-pass surgery is a well known procedure for replacing blood vessels clogged with cholesterol, which will cause the decrease of blood flow in these arteries. It is one of the most commonly performed surgeries in the U.S. for treating heart disease when the coronary arteries are blocked. The general idea behind this procedure is to give the blood a new pathway to the heart.

During coronary artery bypass graft surgery a blood vessel is removed or redirected from one area of the body and placed around the area of narrowing to "bypass" the blockages and restore blood flow to the heart muscle. This vessel is called a graft, and the surgeon will decide which graft to use depending on the location and amount of blockage and the size of the patient's coronary arteries.

The most common bypass grafts used are the internal mammary arteries, as they have been shown to have the best long-term results. In most cases, these arteries can be kept intact at their origin, since they have their own oxygen-rich blood supply. During the procedure, the arteries are sewn to the coronary artery below the site of blockage. This artery is located in the chest and can be accessed through the primary incision for the bypass surgery.

Another graft used is the saphenous vein. These veins are removed from the leg, and then sewn from the aorta to the coronary artery below the site of blockage. Minimally invasive saphenous vein removal may be performed and results in less scarring and a faster recovery.

The technical term used to identify the surgical procedure used to join two hollow organs is anastomosis. Particularly, for bypass surgery, this procedure is performed with suture material, and may be end-to-end side-to-side or end-to-side depending on the circumstances of the required reconstruction or bypass.

Anastomosis is typically performed on blood vessels, arteries and veins. During a typical bypass surgery, the coronary artery is bypassed, and as part of the procedure the fat and tissue must be retracted from the coronary artery to permit viewing and access to the coronary artery during surgery.

There are several fat retractor devices in the prior art. For example, a coronary artery retraction clip for retracting tissue from the coronary artery during coronary anastomosis is known. It comprises a single metal wire forming a central loop spring, first and second supporting arms extending from the loop spring and diverging from each other. At the proximal end of the respective first and second support arms, first and second eyes, and first and second hooks for engaging the tissue to be retracted, the central loop spring, support arms and eyes lying substantially in a single plane, the first and second eyes being formed of the metal wire lying substantially in said plane and configured to receive the tips of forceps substantially perpendicular to said plane, the hooks extending out of said plane and outwardly from the respective arms.

Another known retractor device comprises a single piece of stainless steel wire with a circular spring portion from which two flexible arms are extended. These arms end in a retraction means, which defines a hook-type retracting means for separating the muscle fat from the artery during the procedure.

None of the above mentioned solutions comprise a dual action of tissue retraction and CO2 supplying at the same time. As such, an easy to use disposable coronary artery retraction clip, which can be used with the surgeon's fingers to retract the fat and tissue away from the coronary artery and provide at the same time $CO_2$ directly on the surgical field is still desired in the market.

SUMMARY OF THE INVENTION

A main object of the present invention is to provide a retractor apparatus for use in dissecting mammary arteries during heart by-pass surgery.

Another object of the present invention is to provide a retractor apparatus capable of providing a constant and adjustable flow of $CO_2$ and retracting fat and muscle at the same time on the surgical field during the bypass procedure.

Another object of the present invention is to provide a retractor apparatus cheap and easy to manufacture with an improved capacity for dissecting coronary arteries.

Yet another object of the present invention is to provide a retractor device, including grabbing means that will facilitate the surgeon an easy placement of the retractor around the coronary arteries during the surgical procedure.

Summing up, the present invention is referred to a coronary artery retraction means for retracting tissue and/or fat around the coronary artery during coronary anastomosis. It also includes a CO, supplying device capable of blowing $CO_2$ on the coronary artery to avoid the mixture of air and fluids during a bypass procedure (as CO2 is 30 times more soluble in blood than air), while the retracting means, holds and keeps the fat away from the artery. This device comprises a stainless steel 'V'-shaped wire that includes a couple of elastic arms, which end with a hook-like retracting means. It also includes a grabbing means under the above mentioned arms that allow the surgeon to use the device in an easy and fast maneuver. It also contains a $CO_2$ supplying means on each arm, including at least one gas intake on one end and a gas outlet with a flow nozzle that directs the downward flow of CO2 towards the center of the surgical field over the retracting means, as well as a flow controlling means.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 5 is a general perspective view of a first embodiment of the coronary artery retraction and $CO_2$ dispensing device of the present invention.

DETAILED DESCRIPTION OF REPRESENTATIVE EMBODIMENTS

The main reason for performing a bypass surgery is solving a risky situation in which the arteries that bring blood to the heart muscle (coronary arteries) become clogged by plaque, fat, cholesterol and other substances. This blockage slows or stops blood flow through the heart's blood vessels, and sometimes leads to chest pain or a heart attack. One solution to solve said blockage and thus increasing blood flow to the heart muscle is bypassing the blockage which can relieve chest pain and reduce the risk of heart attack.

During the procedure, surgeons take a segment of a healthy blood vessel from another part of the body and make a detour around the blocked part of the coronary artery. In order to get this segment of a healthy vessel a piece of a leg vein called 'saphenous' may be taken.

Figure 1:
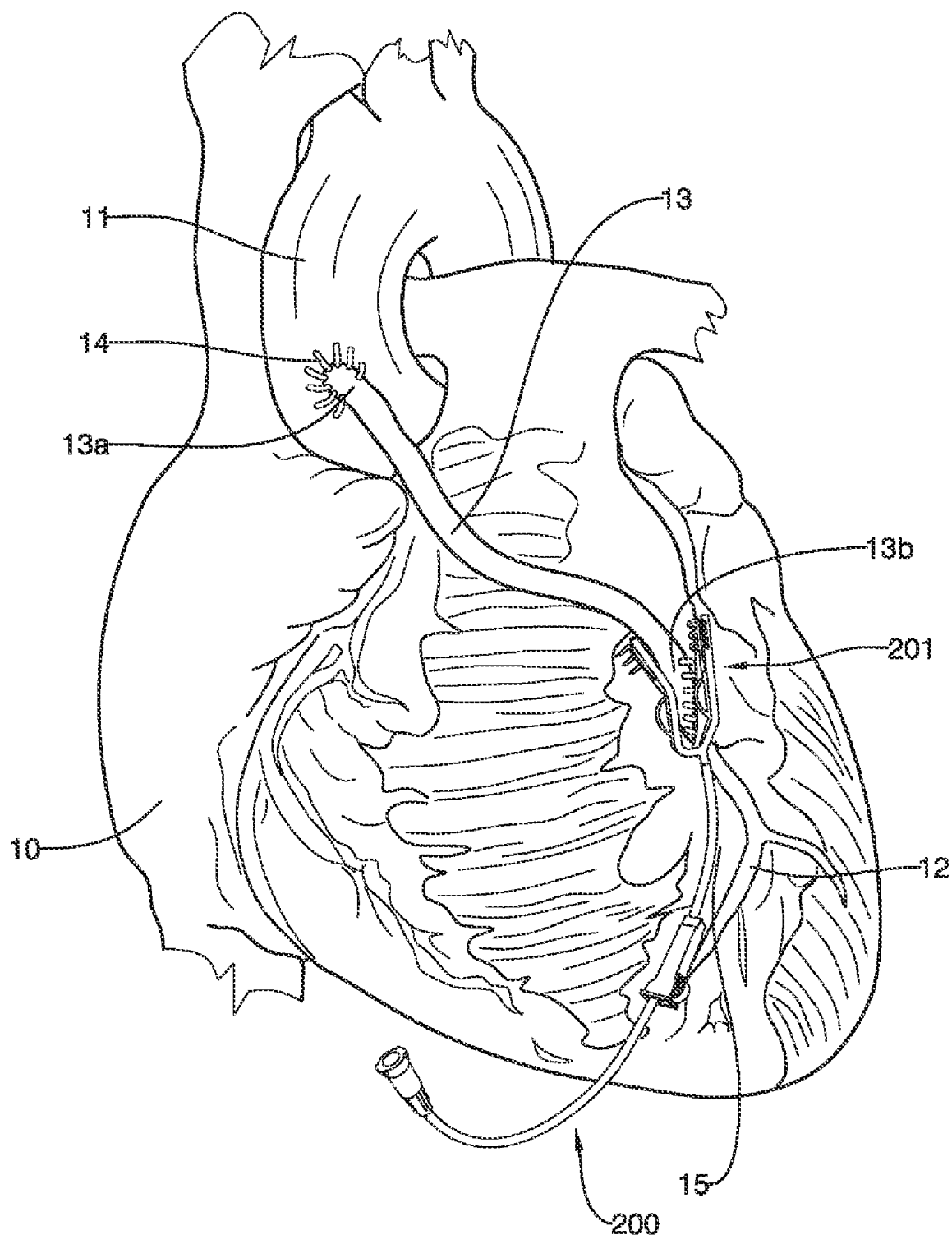
FIG. 1 illustrates a general perspective view of a human heart showing a bypass graft connecting the coronary artery with the aorta as well as fat that the surgeon must retract during the bypass procedure.

Making reference to the attached drawings, FIG. 1 illustrates a typical human heart 10, with the aorta vessel 11 and the coronary artery 12. When said coronary artery 12 is blocked, one end 13a of a healthy vessel 13 is sewn above the blocked area directly on the aorta vessel 11, and the other end 13b of the vein 13 is attached or "grafted" to the coronary artery 12 below the blocked area. Thus, blood can use this new path to flow freely to the heart muscle. The way this vessel or graft 13 is attached to the aorta and the coronary artery are regular stitches 14.

It is extremely important for the surgeon to have the zone of the artery in which the stitches will be done free. As any other muscle, heart is surrounded by fat 15, which sometimes surrounds the coronary artery. Therefore, to perform the bypass the surgeon must retract this fat before starting the procedure on the vessel.

However, considering bypass is an open heart procedure, the patient is completely anesthetized and a pump oxygenator is used. Besides the surgeon, other surgical staff members including a cardiac anesthesiologist, surgical nurse, and a perfusionist (blood flow specialist) participate of the procedure. It is very difficult for other surgical assistants to blow $CO_2$ in a specific location inside the coronary artery during the procedure as in many occasions the surgical field is far from reach. Moreover, a permanent $CO_2$ flow must be directed to the surgical field. Therefore, another staff member must keep the outflow of a $CO_2$ supplying tube blowing constantly on the surgical field. Thus, there are so many 'hands' on a very limited space that may lead to a human error. If the surgeon makes a mistake during the procedure, it may probably cost the patient's life.

This is the reason why the present invention was developed. By using the purposed device, retracting the muscle fat and supplying the necessary $CO_2$ to the surgical field may be done with the same device, avoiding at least the hands of the $CO_2$ supplier on the limited and very sensitive space.

Figure 2:
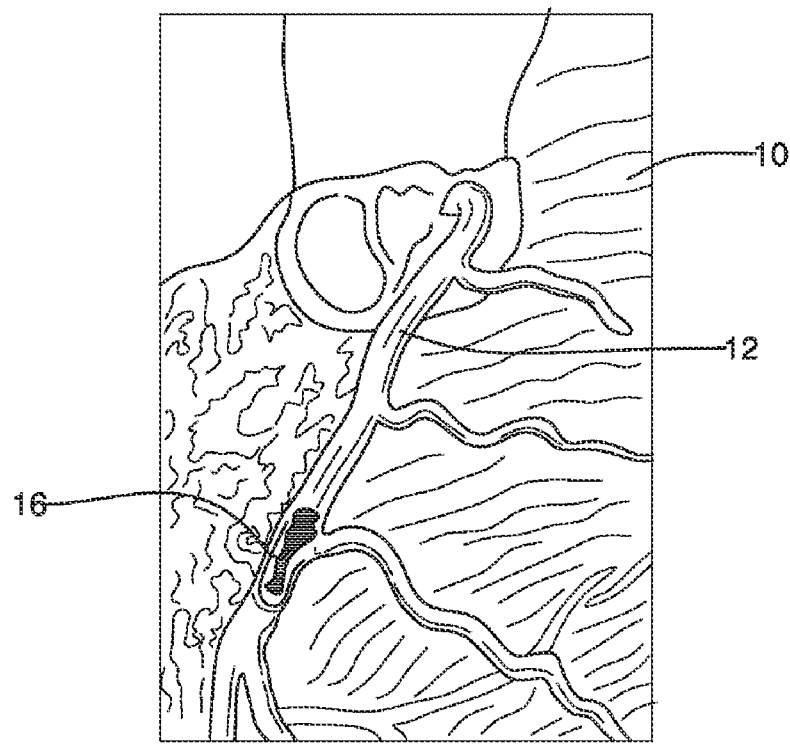
FIG. 2 is another general perspective view of a human heart, this time focusing on the coronary artery, showing schematically the typical blocked coronary that requires a bypass procedure.

FIG. 2 illustrates in more detail the coronary artery and also shows schematically a typical blockage that justifies a bypass procedure. In this case, the blockage 16 represents a dramatic reduction in the blood flow, affecting the patient and putting his/her life at risk.

Figure 3:
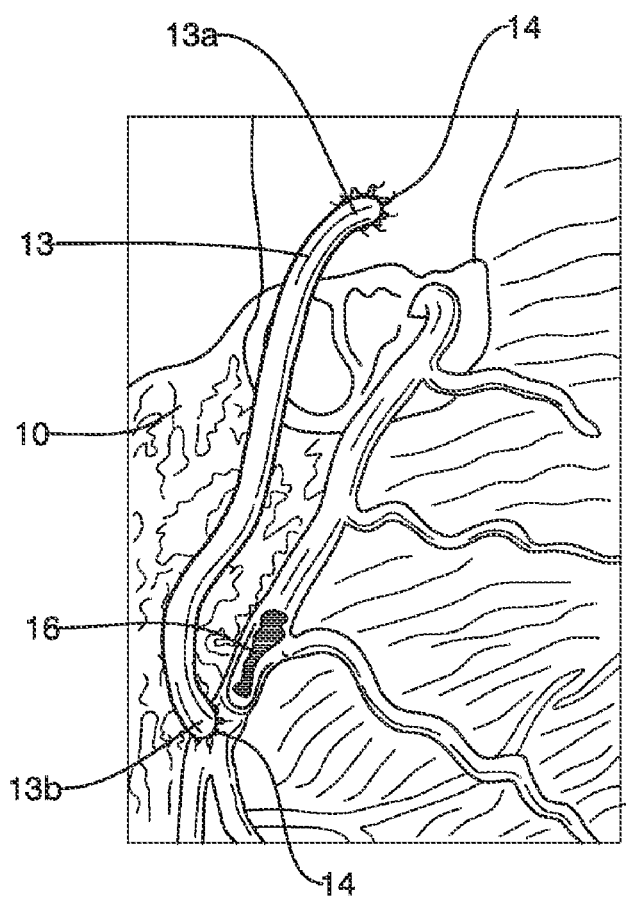
FIG. 3 is another perspective view of the heart, this time showing the vein graft sewn in to bypass a blockage.

FIG. 3 illustrates the same heart after the bypass procedure. As shown, a segment of a healthy vessel that defines a graft 13 was sewn to the coronary artery 12, bypassing blockage 16, and re-routing the blood flow to the heart. Stitches 14 were used to attach the graft 13 to the artery 12.

Figure 4:
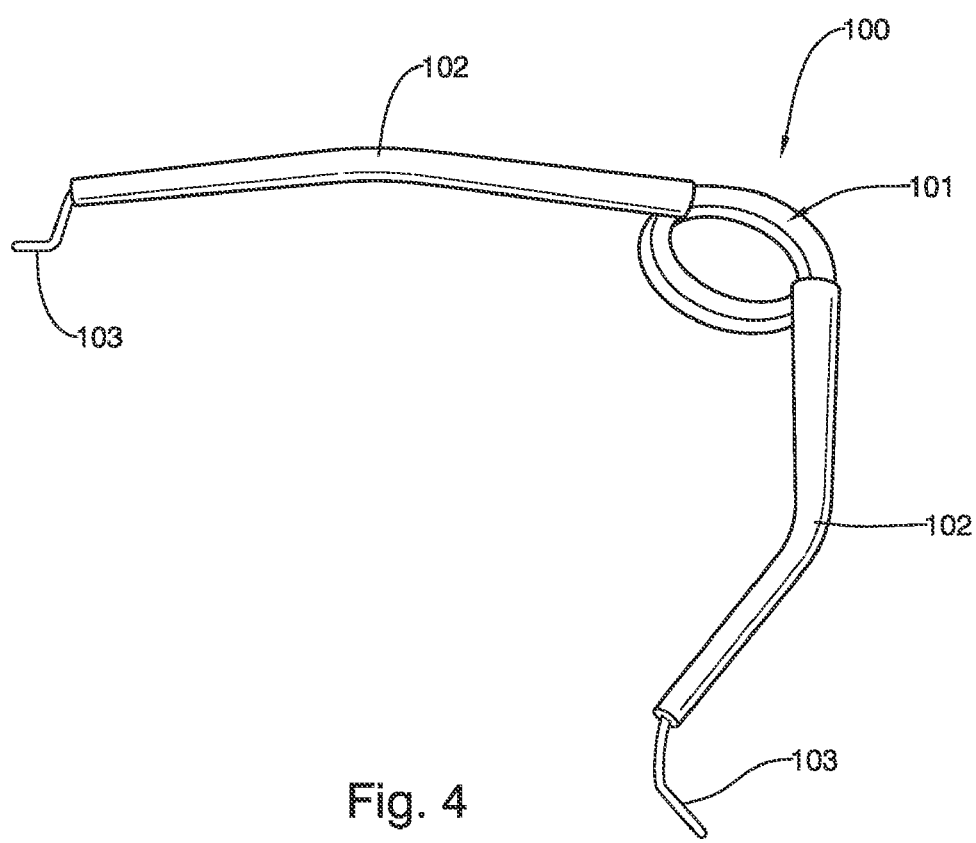
FIG. 4 is a perspective view of a coronary retraction device of the prior art.

FIG. 4 shows a fat retractor 100 of the prior art, manufacture by Genesee BioMedical Inc. under the brand INTRA-ART®. This device comprises a single piece of stainless steel wire with a circular spring portion 101 from which two flexible arms 102 are extended. These arms 102 end in a retraction means 103, which defines a hook-type retracting means for separating the muscle fat from the artery during the procedure. The flexible condition of said arms tends to keep them open. Therefore, when the surgeon places it with the retracting means at each side of the artery in which the graft will be sewn, said arms must be first joined, the retracting means must engage the fat and then after releasing the arms, they create a retracting force on the fat, separating it from the artery and leaving the artery free for the procedure. This device may retract the fatty surface layer over the myocardium to improve the exposure of the coronary artery with a stable retraction provided by two sharpened prongs, which engage the fatty tissue layer.

Even though this type of fat retractor allows an efficient retraction action during the procedure, still demands separate personnel for providing a constant flow of CO2 on the surgical field.

FIG. 5 shows a general perspective view of the purposed device 200. It comprises a single stainless steel V-shaped wire body 201 including a vertex 202 from which two arms 203-204 are divergently extended. Each arm 203-204 comprises a first angled portion 203a-204a from which a generally straight portion 203b-204b is extended. On this straight portion 203b-204b the grabbing means 205 are included. In the illustrated embodiment, grabbing means comprises a rounded handle-like wire portion 205 that extends from the lower side of a portion 203b-204b. This handle allows the surgeon to easily place the fat retractor device in place in an easy and quick maneuver. After said straight portion 203b-204b a final angled portion 203c-204c is extended, which includes the retracting means 206 which, in the illustrated embodiment, comprises three equally-spaced hook-like outwardly-extended teeth 207. These teeth will be responsible of retracting tissue and/or fat from the coronary artery during the procedure.

Over each portion of said wire body 203-204 a hollow tube 208 is extended as an integral part thereof. Said tube comprises on one end a $CO_2$ intake 209 to which a $CO_2$ supplying plastic hose 210 is attached. This tube 208 extends from the gas intake 209 up to the end of said portions 203-204 including a set of downwardly oriented holes 211, which define the $CO_2$ outflow. Over each of said holes, a flow nozzle 212 is located. The position of these holes 211 and the nozzles 212 has a strategic reason. Their orientation leads to a downwardly oriented flow of $CO_2$. Therefore, when this device is in place during the procedure, and the gas flow is open, a stream of CO, will be blowing directly on the surgical field, as required. With this important feature, the present invention avoids the presence of another person during the procedure for keeping the end of a gas blowing hose on the surgical field.

Said $CO_2$ supplying hose 210 includes, at its end 210a, coupling means 220 which, in turn, will be coupled to another coupling means (not illustrated) of another gas supplying hose connected to the gas supplier tube. All these details are not included in the drawings and the present specification as they are not part of the inventive concept presented.

Figure 6:
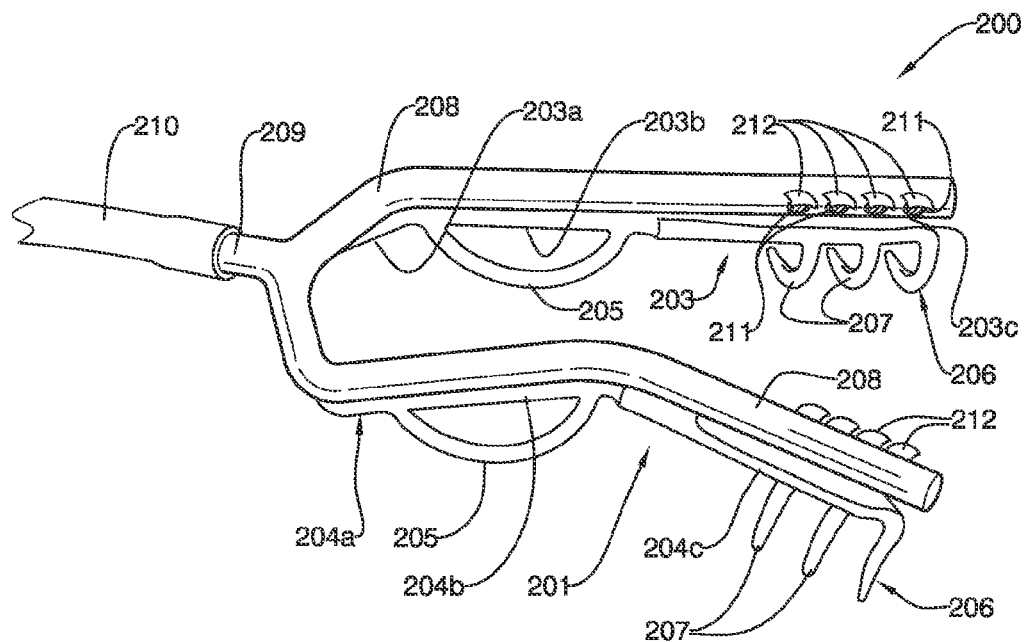
FIG. 6 is a perspective view showing in detail grabbing means of the purposed device that will be used by the surgeon the surgeon to place the blower-retractor device in the surgical field during the bypass surgery.

FIG. 6 shows the purposed device in detail, including intake 209 to which hose 210 is attached. This hose is partially illustrated in this Figure, for more details see FIG. 5. Both arms 203-204 define a single wire body that allows an easy movement between each other for approaching the end portions 203c-204c and then, when they are released, they tend to return to the position shown in this Figure, thus applying a retracting force on the tissue and/or fat during the procedure.

Figure 7:
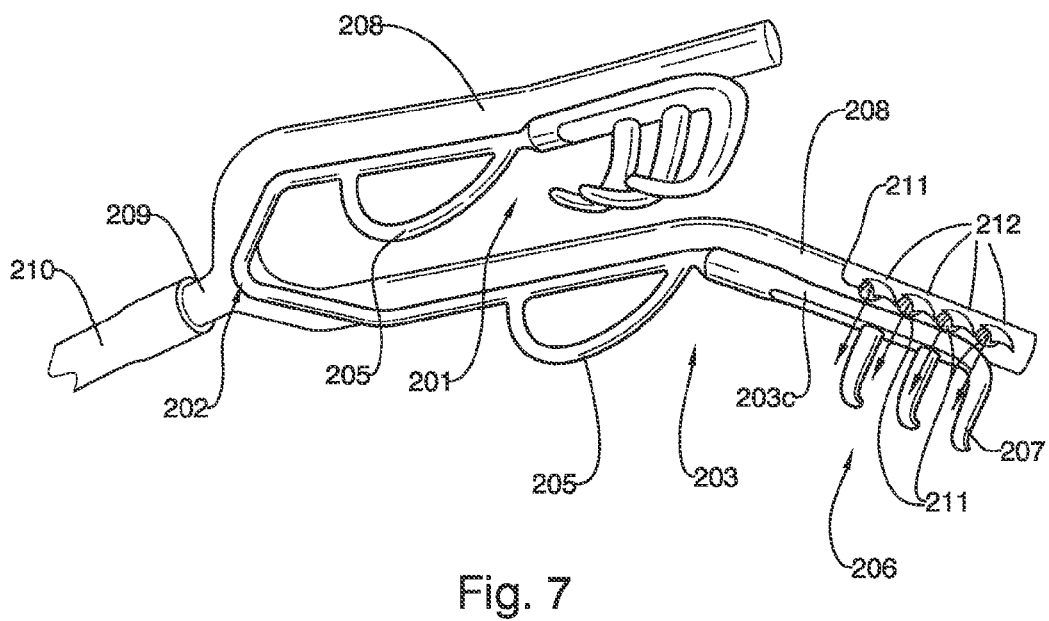
FIG. 7 shows in detail the gas feeding holes and the flow nozzles which direct the $CO_2$ outflow downward towards the center of the surgical field.

FIG. 7 shows a more approached illustration of said retracting means 206 with the curved teeth 207 as well as the gas supplying tube 208 with the downwardly oriented holes 211. In this Figure, a series of downwardly oriented arrows show how the gas is directed towards the surgical field.

Figure 8:
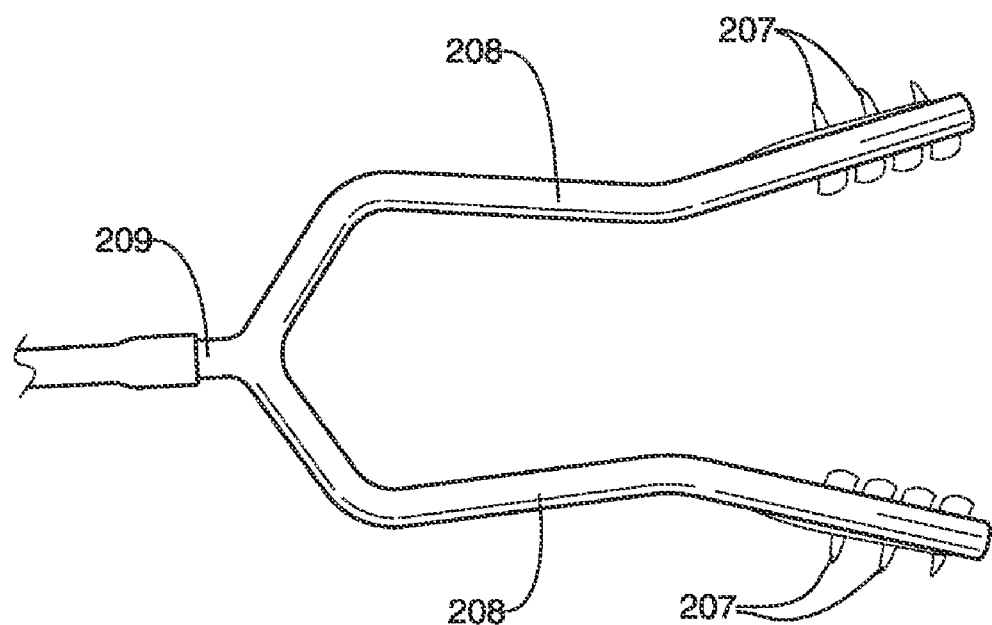
FIG. 8 is a top plan view of the purposed device showing in detail the gas feeding tube and the $CO_2$ connector of the metal body.

FIG. 8 shows a top plan view of the purposed device, showing how the gas supplying tube runs from one end 209 to the other following the pattern defined by the wire body 203-204. It is important to emphasize that said tube is integral with the metal body of portions 203-204 but this should not be understood as a limitation of the present invention. Any skilled person in the art may easily realize these tubes may be replaced by plastic tubes attached or glued to the wire body, without departing from the scope of protection.

Figure 9:
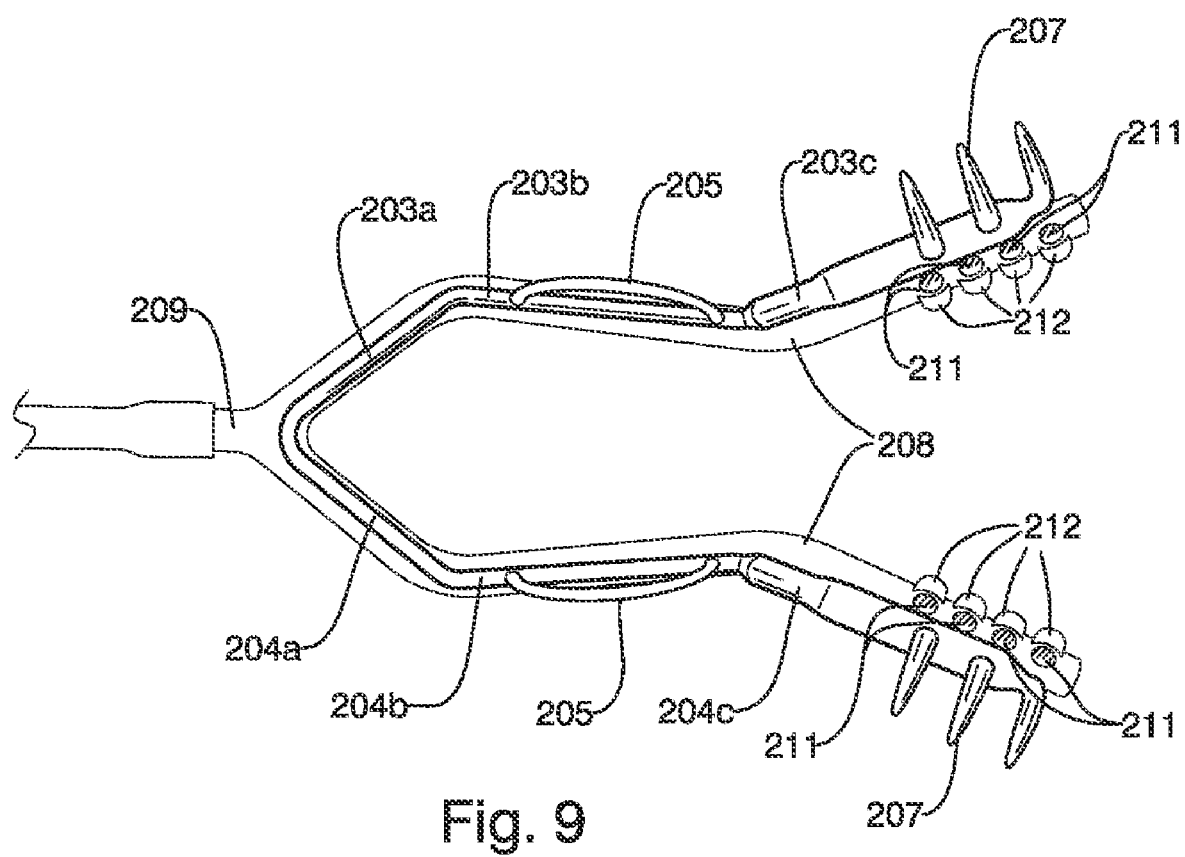
FIG. 9 is a bottom plan view showing the metallic body with the retracting means and the CO2 outflows.

FIG. 9 shows a bottom plan view of the purposed device, showing in detail every portion of the wire body 203-204 as well as teeth 207 and the gas intake 209 to which the gas supplying hose 210 is attached. Said supplying hose 210 may include a flow regulator 213. There are several known flow regulators in the market, and in the illustrated case it comprises a carcass in which a regulating wheel is installed. Thus the surgeon or one of his/her assistants may regulate the $CO_2$ flow during the procedure by simply rotating said wheel.

Figure 10:
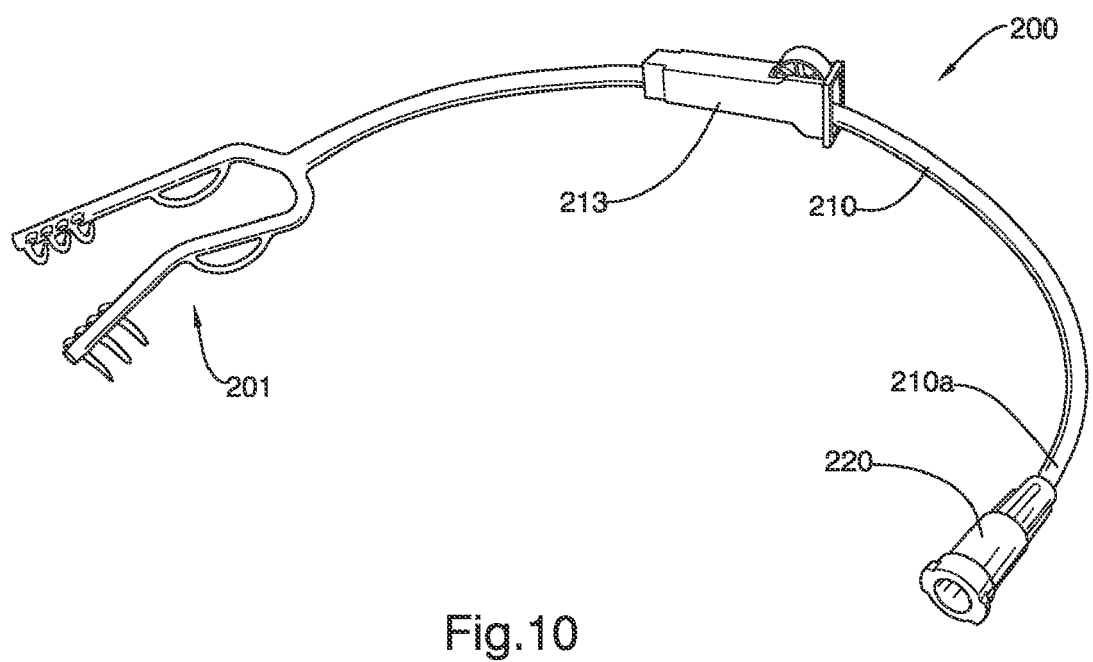
FIG. 10 is a general perspective view of a second embodiment of the coronary artery retraction and $CO_2$ dispensing device of the present invention.

FIG. 10 illustrates a second embodiment of the artery retraction means of the present invention. In this case, the whole device is made of the same plastic material: the V-shape piece, the gas feeding tube and the feeding hose. All these parts are an integral part of a whole and single plastic piece. As it is clearly illustrated, the device comprises the same parts, but instead of combining metal parts with plastic parts as in the previous embodiment, in this case all the parts are plastic and the device is fully disposable after the surgery.

Figure 11:
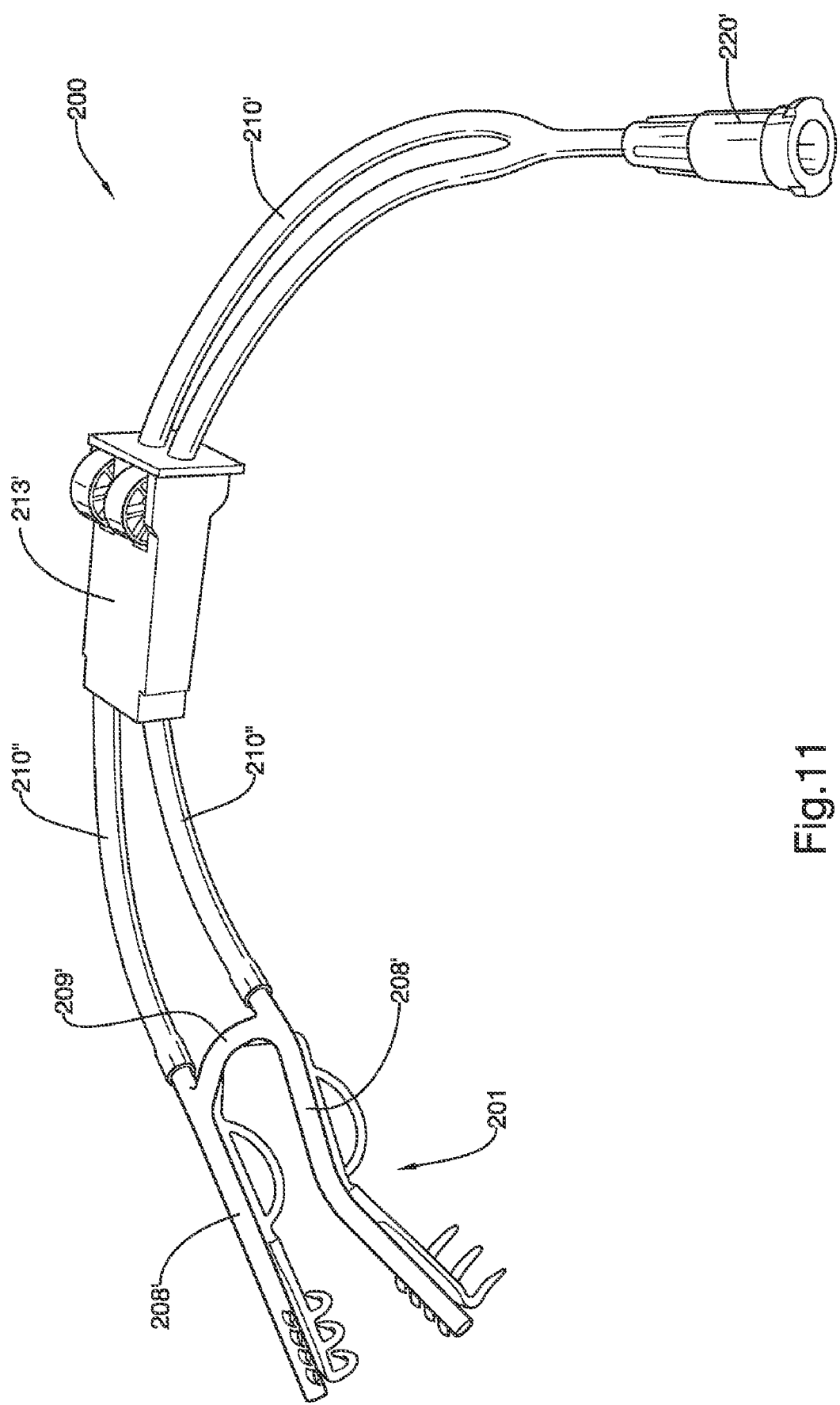
FIG. 11 is another perspective view of another embodiment of the bypass graft in accordance with the present invention.

FIG. 11 shows another perspective view of a second embodiment in which the device 200 includes a U-shaped wire body 201 including a rounded vertex 209' from which two arms 208' are divergently extended. Said portion 209' includes two inlets to which respective hoses 210' are connected. The gas flow in both hoses 210' are regulated by a single regulator 213' that includes two regulating wheels. Each wheel is capable of regulating the flow in each hose independently. From the regulator two final portions of said hoses 210' are extended and merge on a single hose. At the end a coupler 220' is included to connect this device to the gas supplying tank (not illustrated).

The present device 200 has different sizes for accommodating the surgical needs of different heart sizes. There are variations from 1⅞" or 1½" to 1". Both variations will be available in all sizes and will be disposable too.

While the preferred embodiments of the invention have been described above, it will be recognized and understood that various modifications can be made in the invention, and the appended claims are intended to cover all such modifications which may fall within the spirit and scope of the invention.

I claim:

1. Coronary artery retraction and $CO_2$ dispensing device for retracting tissue and/or fat around and inside the coronary artery during coronary anastomosis and a $CO_2$ supplying device capable of blowing $CO_2$ on the coronary artery during a bypass procedure while the retracting means holds and keeps the fat away from the artery; the device comprising a wire including a couple of elastic arms including a couple of hook-like retracting means attached separately to each arm extending first downwards and then outwards away from a central region of the device, a couple of grabbing means shaped as rounded wire portions extending from the lower side of each elastic arm beginning and terminating separately on each arm such that the grabbing means are not directly in contact with the retracting means, and a $CO_2$ supplying means on each arm including at least one gas intake on one end and a gas outlet over said retracting means.

2. The coronary artery retraction and $CO_2$ dispensing device of claim 1, wherein the wire is made of stainless steel.

3. The coronary artery retraction and $CO_2$ dispensing device of claim 1, wherein the hook-like retracting means comprises a set of three aligned curved teeth.

4. The coronary artery retraction and $CO_2$ dispensing device of claim 1, wherein the grabbing means is defined by a rounded handle-like wire portion that extends from the lower side of the elastic arms.

5. The coronary artery retraction and $CO_2$ dispensing device of claim 1, wherein the gas outlet comprises a set of holes on the inner portion of each elastic arm.

6. The coronary artery retraction and $CO_2$ dispensing device of claim 1, wherein the wire is made of surgical steel.

7. The coronary artery retraction and $CO_2$ dispensing device of claim 1, wherein the wire has a "V" shape.

8. The coronary artery retraction and $CO_2$ dispensing device of claim 7, wherein each elastic arm comprises a hollow conduit that merge on a single hollow gas inlet.

9. The coronary artery retraction and $CO_2$ dispensing device of claim 8, wherein the $CO_2$ supplying means is defined by a gas supplying hose connected to said gas inlet and to a $CO_2$ dispensing tank.

10. The coronary artery retraction and $CO_2$ dispensing device of claim 9, wherein said gas supplying hose includes a flow regulator means.

11. The coronary artery retraction and $CO_2$ dispensing device of claim 10, wherein said flow regulator means includes a hollow carcass and a regulating wheel rotatable attached thereto.

12. The coronary artery retraction and $CO_2$ dispensing device of claim 10, wherein said flow regulator means includes a hollow carcass and a regulating wheel rotatable attached thereto.

13. The coronary artery retraction and $CO_2$ dispensing device of claim 12, wherein over each of said holes, a flow nozzle is located.

14. The coronary artery retraction and $CO_2$ dispensing device of claim 10, wherein to each hose a gas flow regulating wheel is connected.

15. The coronary artery retraction and $CO_2$ dispensing device of claim 9, wherein the $CO_2$ dispensing means includes a connector capable of connecting the gas supplying hose to the gas tank.

16. The coronary artery retraction and $CO_2$ dispensing device of claim 1, wherein the wire has a "U" shape.

17. The coronary artery retraction and $CO_2$ dispensing device of claim 16, wherein each elastic arm comprises a hollow conduit each of which includes a gas inlet portion.

18. The coronary artery retraction and $CO_2$ dispensing device of claim 17, wherein the $CO_2$ supplying means is defined by two gas supplying hoses connected to each gas inlet and to a $CO_2$ dispensing tank.

19. The coronary artery retraction and $CO_2$ dispensing device of claim 18, wherein said gas supplying hose includes one flow regulator means for each hose.

20. Coronary artery retraction and $CO_2$ dispensing device for retracting tissue and/or fat around and inside the coronary artery during coronary anastomosis and a $CO_2$ supplying device capable of blowing $CO_2$ on the coronary artery during a bypass procedure while the retracting means holds and keeps the fat away from the artery; the device comprising a "V" shaped wire including a couple of elastic arms including hook-like retracting means, grabbing means, and a $CO_2$ supplying means on each arm including at least one gas intake on one end and a gas outlet over said retracting means wherein each elastic arm comprises a hollow conduit that merge on a single hollow gas inlet and further wherein the $CO_2$ supplying means is defined by a gas supplying hose connected to said gas inlet and to a $CO_2$ dispensing tank and wherein said gas supplying hose includes a flow regulator means and wherein to each hose a gas flow regulating wheel is connected and wherein each nozzle defines a downwardly oriented curved cover capable of directing the flow of gas towards the surgical field.

\* \* \* \* \*